US012727743B2

(12) United States Patent
Bec et al.

(10) Patent No.: US 12,727,743 B2
(45) Date of Patent: Sep. 8, 2026

(54) BROADBAND, FREEFORM FOCUSING MICRO OPTICS FOR SIDE-VIEWING IMAGING CATHETERS

(71) Applicant: The Regents of the University of California, Oakland, CA (US)

(72) Inventors: Julien Bec, Davis, CA (US); Laura Marcu, Davis, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 837 days.

(21) Appl. No.: 18/086,462

(22) Filed: Dec. 21, 2022

(65) Prior Publication Data

US 2023/0136729 A1 May 4, 2023

Related U.S. Application Data

(63) Continuation of application No. 16/648,210, filed as application No. PCT/US2018/060863 on Nov. 13, 2018, now abandoned.

(Continued)

(51) Int. Cl.

*A61B 1/00* (2006.01)
*A61B 1/04* (2006.01)

(Continued)

(52) U.S. Cl.

CPC ........ *A61B 1/00177* (2013.01); *A61B 1/0011* (2013.01); *A61B 1/00165* (2013.01); *A61B 1/043* (2013.01); *A61B 1/051* (2013.01); *A61B 5/0084* (2013.01); *A61B 5/6852* (2013.01); *A61B 8/12* (2013.01); *A61B 8/4416* (2013.01);

(Continued)

(58) Field of Classification Search

CPC .. G02B 6/3512; A61B 1/0011; A61B 1/00177
See application file for complete search history.

(56) References Cited

U.S. PATENT DOCUMENTS

2011/0137124 A1* 6/2011 Milner ................ A61B 5/6852 600/160
2012/0091551 A1* 4/2012 Marenco .............. H10F 39/024 257/E31.127

(Continued)

FOREIGN PATENT DOCUMENTS

WO WO-2014120588 A1 * 8/2014 ............ G02B 6/423

*Primary Examiner* — Charlie Y Peng
(74) *Attorney, Agent, or Firm* — MARSHALL, GERSTEIN & BORUN LLP

(57) ABSTRACT

The disclosed embodiments relate to a system that implements a side-viewing imaging catheter. This system includes a catheter sheath enclosing an imaging core, wherein the imaging core resents an internal optical channel coupled to an optical element located at the distal end of the imaging core. The optical element includes an internal reflective surface that reflects and focuses light transmitted via the optical channel in a direction orthogonal to a rotational axis of the catheter toward a target location, and returns reflected light from the target location back through the optical channel. This internal reflective surface of the optical element is shaped to focus the light so that a resulting beam shape at the target location has a small cross section area and substantially equal axial and transaxial dimensions.

14 Claims, 7 Drawing Sheets

Related U.S. Application Data

(60) Provisional application No. 62/586,728, filed on Nov. 15, 2017.

(51) Int. Cl.

| | |
|---|---|
| ***A61B 1/05*** | (2006.01) |
| ***A61B 5/00*** | (2006.01) |
| ***A61B 8/00*** | (2006.01) |
| ***A61B 8/12*** | (2006.01) |
| ***C03C 25/6208*** | (2018.01) |

(52) U.S. Cl.
CPC ........ *A61B 8/4494* (2013.01); *C03C 25/6208* (2018.01)

(56) References Cited

U.S. PATENT DOCUMENTS

2019/0086609 A1* 3/2019 Shaw ................ H01L 21/67092
2020/0170702 A1* 6/2020 Warnking .......... A61B 18/1492

* cited by examiner

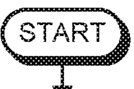

CREATE ONE OR MORE CURVED SURFACES IN A SILICA WAFER, WHEREIN THE ONE OR MORE CURVED SURFACES HAVE A GEOMETRY SUITABLE TO SHAPE AN INTERNAL OPTICAL BEAM BY REFLECTION
502

DEPOSIT A REFLECTIVE COATING ON THE SILICA WAFER TO PROVIDE REFLECTIVITY, THEREBY CONVERTING THE ONE OR MORE CURVED SURFACES INTO ONE OR MORE INTERNAL FREEFORM REFLECTIVE SURFACES
504

CUT THE SILICA WAFER TO OBTAIN ONE OR MORE MICRO-OPTIC ELEMENTS, WHICH ARE CONFIGURED TO RECEIVE AN INCOMING OPTICAL BEAM ALONG A ROTATIONAL AXIS OF THE CATHETER, WHEREIN EACH MICRO-OPTIC ELEMENT INCLUDES A FREEFORM REFLECTIVE INTERNAL SURFACE TO REFLECT THE INCOMING OPTICAL BEAM IN A SUBSTANTIALLY ORTHOGONAL DIRECTION FROM THE OPTICAL AXIS TOWARD A TARGET LOCATION, WHEREIN THE INTERNAL REFLECTIVE SURFACE IS SHAPED TO FOCUS THE BEAM SO THAT A RESULTING BEAM SHAPE AT THE TARGET LOCATION HAS SUBSTANTIALLY EQUAL AXIAL AND TRANSAXIAL DIMENSIONS
506

END

FIG. 5

BROADBAND, FREEFORM FOCUSING MICRO OPTICS FOR SIDE-VIEWING IMAGING CATHETERS

CROSS-REFERENCE TO RELATED APPLICATION

This application is a continuation of U.S. patent application Ser. No. 16/648,210 which was filed Mar. 17, 2020 (the '210 application). The '210 application is a 371 of PCT/US2018/060863, which was filed on Nov. 13, 2018 (the '060863 application). The '060863 application claims the benefit of U.S. Provisional Patent Application No. 62/586,728, which was filed on Nov. 15, 2017. The contents of the preceding applications are incorporated by reference herein.

GOVERNMENT LICENSE RIGHTS

This invention was made with U.S. government support under grant no. HL67377, awarded by the National Institutes of Health. The U.S. government has certain rights in the invention.

BACKGROUND

Field

The disclosed embodiments generally relate to catheter-based vascular-imaging systems. More specifically, the disclosed embodiments relate to the design of broadband, freeform micro optics for side-viewing imaging catheters.

Related Art

Imaging catheters and endoscopes are presently the focus of significant research effort, with diagnostic applications in the fields of cardiovascular medicine, gastroenterology and pulmonology. Catheter-based optical imaging modalities share common characteristics, such as a fiber for delivery of light to tissue, distal optical elements to direct and focus the beam, and a transparent sheath surrounding the device. A number of research groups have recently developed multimodal devices, which include a morphological imaging modality, such as optical coherence tomography (OCT) or intravascular ultrasound (IVUS), combined with fluorescence or spectroscopic techniques that provide additional composition information.

In the cardiovascular field, pulse sampling fluorescence lifetime imaging (FLIm) provides great potential for characterizing tissue biochemical information, because it is able to provide information related to inflammation as well as changes in protein content. (See L. Marcu, J. A. Jo, Q. Fang, T. Papaioannou, T. Reil, J.-H. Qiao, J. D. Baker, J. A. Freischlag, and M. C. Fishbein, "Detection of rupture-prone atherosclerotic plaques by time-resolved laser-induced fluorescence spectroscopy," Atherosclerosis 204, 156-164 (2009). This is achieved without the use of exogenous molecular probes, making it a good candidate for clinical translation. A FLIm implementation differs from existing modalities such as OCT in terms of the wavelength range as well as the type of fiber used for light delivery and collection. Excitation is typically performed in the near ultraviolet (UV) range to match the absorption range of many biological fluorophores. An excitation wavelength of 355 nm is commonly used due to the availability of sub-nanosecond pulse diode pumped solid state lasers working at this wavelength. Additionally, fluorescence photons need to be efficiently collected leading to the use of large core multimode fibers (>100 μm). These additional constraints make two commonly used distal-end optics designs, namely gradient index (GRIN) lenses and ball lenses poorly suited for FLIm.

GRIN lenses are used for a variety of applications in the visible and near-infrared range. However, commonly used dopants, such as sliver ions, present strong absorption and autofluorescence at 355 nm. UV-compatible dopants such as lithium are available, but limits in their refractive index variations lead to a low numerical aperture (NA) (around 0.2). This low NA leads to relatively long (>3 mm) elements, which are unsuitable for vascular applications. Additional limitations are strong chromatic aberrations and an optical index profile that presents a circular symmetry and, therefore, does not enable the correction of astigmatism introduced by the device sheath, which leads to different focal distances in the axial and transaxial directions.

Another implementation of a distal-end optic comprises a fused ball lens, where a short section of no-core fiber is spliced with the main fiber and fused into a spheroid. The spheroid is polished to provide an angled facet that deflects the beam via total internal reflection. With this design, different radii can be obtained in the axial and transaxial directions to correct for the astigmatism introduced by the device sheath. A suitable geometry of the spheroid is achieved empirically by optimizing the fusion process.

However, a ball lens termination for a large core multimode fiber (>100 μm) requires the splicing of a larger no-core fiber to perform beam expansion, which is itself fused into a sphere. Moreover, the longer heating period required for large spheres (>~300 μm) leads to sagging during the heating process, which causes an asymmetry of the geometry. Additionally, the use of the probe in liquids requires capping with a short length of glass capillary because both total internal reflection from the facet and focusing from the surface of the spheroid relies on a glass-to-air interface. Moreover, capping introduces additional astigmatism and increases bulk and complexity.

Hence, what is needed is a distal-end side-viewing micro optic that facilitates excitation of a sample in the near UV range without the drawbacks of existing micro optic designs.

SUMMARY

The disclosed embodiments relate to a system that implements a side-viewing imaging catheter. This system includes a catheter sheath enclosing an imaging core, wherein the imaging core presents an internal optical channel coupled to an optical element located at the distal end of the imaging core. The optical element includes an internal reflective surface that reflects and focuses light transmitted via the optical channel in a direction orthogonal to a rotational axis of the catheter toward a target location, and returns reflected light from the target location back through the optical channel This internal reflective surface of the optical element is shaped to focus the light so that a resulting beam shape at the target location has a small cross section area and substantially equal axial and transaxial dimensions.

In some embodiments, a shape of the internal reflective surface is numerically computed by optimizing a polynomial surface to minimize a radius of the beam shape at the target location.

In some embodiments, the internal reflective surface comprises an aspheric surface with additional polynomial aspheric terms.

In some embodiments, the internal reflective surface is fabricated through direct-write laser machining in combination with a secondary surface reflow operation.

In some embodiments, the internal reflective surface is shaped to reflect the light with a beam tilt in a forward axial direction.

In some embodiments, the optical element includes a reflective coating to provide broadband reflectivity.

In some embodiments, the side-viewing imaging catheter is configured to perform ultraviolet (UV) imaging.

In some embodiments, the optical element is comprised of fused silica.

In some embodiments, the side-viewing imaging catheter is a multimodal catheter, which supports both optical and ultrasonic imaging, wherein the catheter tube additionally encloses an electrical channel, and wherein the probe additionally includes an ultrasonic transducer coupled to the electrical channel This ultrasonic transducer is oriented orthogonally to a rotational axis of the catheter and is configured to generate an ultrasonic acoustic signal and to return resulting echo information.

In some embodiments, the multimodal catheter supports both intravascular ultrasound imaging and multispectral fluorescence-lifetime imaging microscopy.

The disclosed embodiments also relate to a process for manufacturing a side-viewing micro optic. During this process, one or more curved surfaces are created in a silica wafer, wherein the one or more curved surfaces have a geometry suitable to shape an internal optical beam by reflection. Next, a reflective coating is deposited on the silica wafer to provide reflectivity, thereby converting the one or more curved surfaces into one or more internal freeform reflective surfaces. Finally, the silica wafer is cut to obtain one or more micro-optic elements, which are configured to receive an incoming optical beam along a rotational axis of the catheter, wherein each micro-optic element includes a freeform reflective internal surface to reflect the incoming optical beam in a substantially orthogonal direction from the optical axis toward a target location, wherein the internal reflective surface is shaped to focus the beam so that a resulting beam shape at the target location has substantially equal axial and transaxial dimensions.

In some embodiments, the one or more curved surfaces are created using direct laser machining.

In some embodiments, the one or more curved surfaces are created using a grayscale lithography technique.

In some embodiments, the reflective coating is not deposited in cases where a total internal reflection with a surrounding medium is sufficient to reflect the optical beam.

In some embodiments, creating the one or more curved surfaces involves creating a microlens array comprising a large number of curved surfaces organized in a rectangular pattern on the silica wafer.

In some embodiments, the cutting of the silica wafer is performed using a dicing saw. This process involves: mounting the coated silica wafer on a silicon wafer using mounting media; cutting the microlens array along a vertical direction of the microlens array to create individual strips of microlenses; removing each microlens strip from the silicon wafer by heating the mounting media; positioning and securing each microlens strip so that a side of the microlens strip is attached to a second silicon wafer using mounting media; using a dicing saw to cut each microlens strip into individual microlenses; and performing a trimming operation on each microlens to obtain a specified length.

In some embodiments, performing the trimming operation on each microlens involves: removing the microlens from an underlying wafer; mounting the microlens on a support such that the only part to be removed protrudes from the support; and polishing the microlens to a specified length.

In some embodiments, the cutting of the silica wafer is performed using a laser.

In some embodiments, the cutting of the silica wafer is performed in a single operation by tilting a cutting plane.

In some embodiments, the process also involves polishing an upper surface of each microlens to limit scattering caused by roughness created by the dicing process.

In some embodiments, while using the direct laser machining process to create the microlens array, the process ensures that a spacing between microlenses corresponds to a kerf width of a blade of the dicing saw.

BRIEF DESCRIPTION OF THE FIGURES

FIG. 5 presents a flowchart illustrating a process for fabricating micro-optic elements in accordance with disclosed embodiments.

DETAILED DESCRIPTION

The following description is presented to enable any person skilled in the art to make and use the present embodiments, and is provided in the context of a particular application and its requirements. Various modifications to the disclosed embodiments will be readily apparent to those skilled in the art, and the general principles defined herein may be applied to other embodiments and applications without departing from the spirit and scope of the present embodiments. Thus, the present embodiments are not limited to the embodiments shown, but are to be accorded the widest scope consistent with the principles and features disclosed herein.

The data structures and code described in this detailed description are typically stored on a computer-readable storage medium, which may be any device or medium that can store code and/or data for use by a computer system. The computer-readable storage medium includes, but is not limited to, volatile memory, non-volatile memory, magnetic and optical storage devices such as disk drives, magnetic tape, CDs (compact discs), DVDs (digital versatile discs or digital video discs), or other media capable of storing computer-readable media now known or later developed.

The methods and processes described in the detailed description section can be embodied as code and/or data, which can be stored in a computer-readable storage medium as described above. When a computer system reads and executes the code and/or data stored on the computer-readable storage medium, the computer system performs the methods and processes embodied as data structures and code and stored within the computer-readable storage medium. Furthermore, the methods and processes described below can be included in hardware modules. For example, the hardware modules can include, but are not limited to, application-specific integrated circuit (ASIC) chips, field-programmable gate arrays (FPGAs), and other programmable-logic devices now known or later developed. When the hardware modules are activated, the hardware modules perform the methods and processes included within the hardware modules.

Technical Details

Figure 1A:
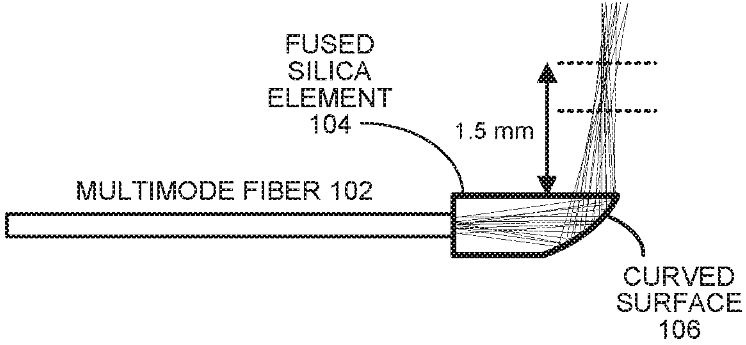
FIG. 1A illustrates a reflective micro optic that facilitates both beam focusing and reflection in accordance with disclosed embodiments.

As is illustrated in FIG. 1A, the reflective micro optic, which was developed to address these challenges, comprises a fused silica element 104 terminated by a curved surface 106 with a reflective coating that performs both beam focusing and reflection operations for an optical beam that originates from a multimode fiber 102. This design is inherently broadband because the optical beam is transmitted through pure glass and reflections are not subject to chromatic aberrations. An important aspect of the performance of the proposed solution is to be able to fully specify the geometry of the reflective optical surface. This is because different radii of curvature are required to achieve an identical focal plane in the axial and transaxial directions at a target location, and astigmatisms introduced by other elements in the beam path such as the device's sheath need to be corrected.

Figure 1B:
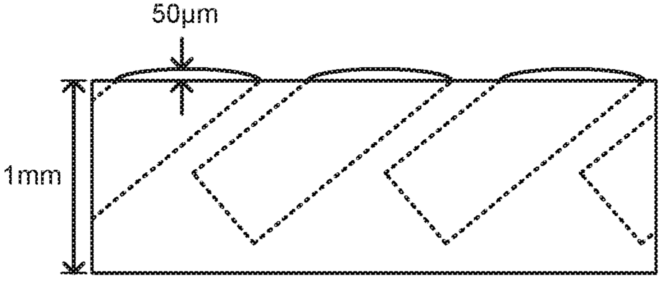
FIG. 1B illustrates how a reflective micro optic is cut from a silica wafer in accordance with disclosed embodiments.

Direct-write laser machining of a fused silica substrate, such as LightForge (PowerPhotonic, Fife, UK), enables the manufacture of such freeform surfaces. (See Matthew Currie and Roy McBride, "Rapid manufacture of freeform micro-optics for high power applications," Proc. SPIE 8970, Laser 3D Manufacturing, 89700T (6 Mar. 2014); doi: 10.1117/12.2040140.) In combination with a secondary surface reflow operation, highly smooth optical surfaces with micrometer accuracy can be manufactured over a clear aperture of 15×15 mm$^2$, provided the design presents a sag of less than 50 μm and a slope of less than 45 degrees. Note that the machining depth is much smaller than the expected size of the optics, so to comply with these manufacturing constraints, the simulated freeform element is positioned such that the freeform surface is tangential to a horizontal plane and therefore fully fits within a 50 μm height as is illustrated in FIG. 1B. Subsequent cutting with a dicing saw is used to separate the optics from the rest of the substrate.

A reflective surface, which is compatible with these constraints, was computed using Zemax (Radiant, Redmond, WA). The simulated model included a fully filled 0.22 NA, 100 μm core multimode fiber and a UV-fused silica optical element having a 300×300 μm$^2$ cross section. The freeform reflective surface was defined as a conic aspheric surface with additional polynomial aspheric terms, and was numerically optimized to provide a 10-degree forward beam tilt and to minimize the beam RMS radius at 1.5 mm distance as is illustrated in FIG. 1A.

For efficient manufacturing, a microlens-like array replicating the freeform surface to fully fill the clear aperture was created in Zemax. The pitch in both directions was set such that the clearance between each of the micro optics corresponds to the width of the 100 μm wide dicing blade (2.187-4A-30RU7-3, Thermocarbon, Inc., Casselberry, FL, USA). The design file was then converted for manufacturing into an array that defines the surface height data over a rectangular 10 μm pitch grid with a Zemax macro provided by PowerPhotonic. After laser machining, a UV-enhanced aluminum coating was applied to provide broadband reflectivity in the UV-visible range (Laseroptik, Garbsen, Germany). Individual micro optics were obtained by a two-step dicing operation, wherein the array was first mounted onto a 4" silicon wafer with temporary adhesive (Crystalbond 590, Electron Microscopy Sciences, Hatfield, PA, USA), and then cuts were made between optics columns to create strips. Individual strips were then removed and mounted on their side on a second wafer using temporary adhesive, and were then aligned and diced. The resulting individual optics were then mounted on a support using temporary adhesive and polished to length using diamond lapping sheets (LFXD, Thorlabs, Newton, NJ, USA) before final integration into a device.

Figure 2:
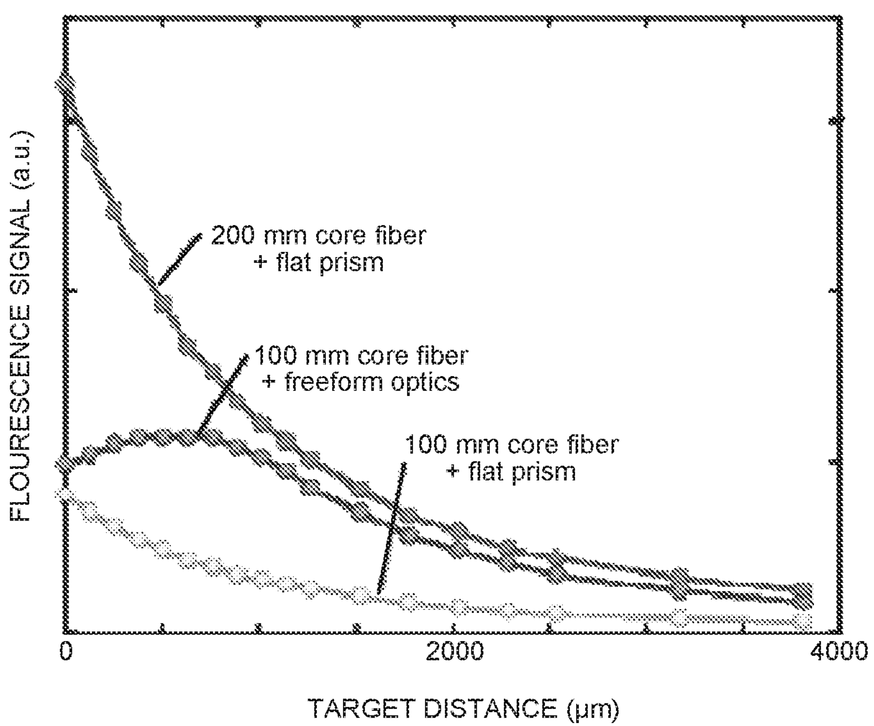
FIG. 2 presents a graph illustrating variations of a fluorescence signal as a function of distance for both a freeform optic and a flat prism in accordance with disclosed embodiments.

The freeform optics were assembled at the distal end of 100 μm core fiber optic (FVP100110125, Polymicro Technologies, Phoenix, AZ, USA) using acrylate optical adhesive (OG603, Epoxy Technology, Inc., Billerica, MA, USA). This probe was connected to the FLIm system to perform the experimental characterization of the fluorescence signal intensity with respect to distance. (See D. Ma, J. Bec, D. R. Yankelevich, D. Gorpas, H. Fatakdawala, and L. Marcu, J. Biomed. Opt. 19, 2014.) A 150 μm thick polystyrene sheet was used as a target. The combination of the 100 mm core fiber and the freeform optic was compared with existing 100 μm and 200 μm fibers terminated with flat prisms. See FIG. 2, which illustrates the resulting variations of the fluorescence signal as a function of distance for the freeform optic as well as a flat prism. Note that for distances above 1 mm, the freeform optic in combination with a 100 μm core fiber provides results close to that of a 200 μm core fiber despite a fourfold reduction in fiber cross section. Moreover, the collection efficiency obtained with the micro optics is almost on par with the collection efficiency of a 200 μm fiber (83% at 1 mm distance) despite the fourfold reduction in fiber cross section, and results in a lower variation of signal as a function of distance: the ratio of signal at a 3 mm distance to the maximum signal is 23.5% and 11% respectively, leading to improvements in signal uniformity during scanning.

Figure 3:
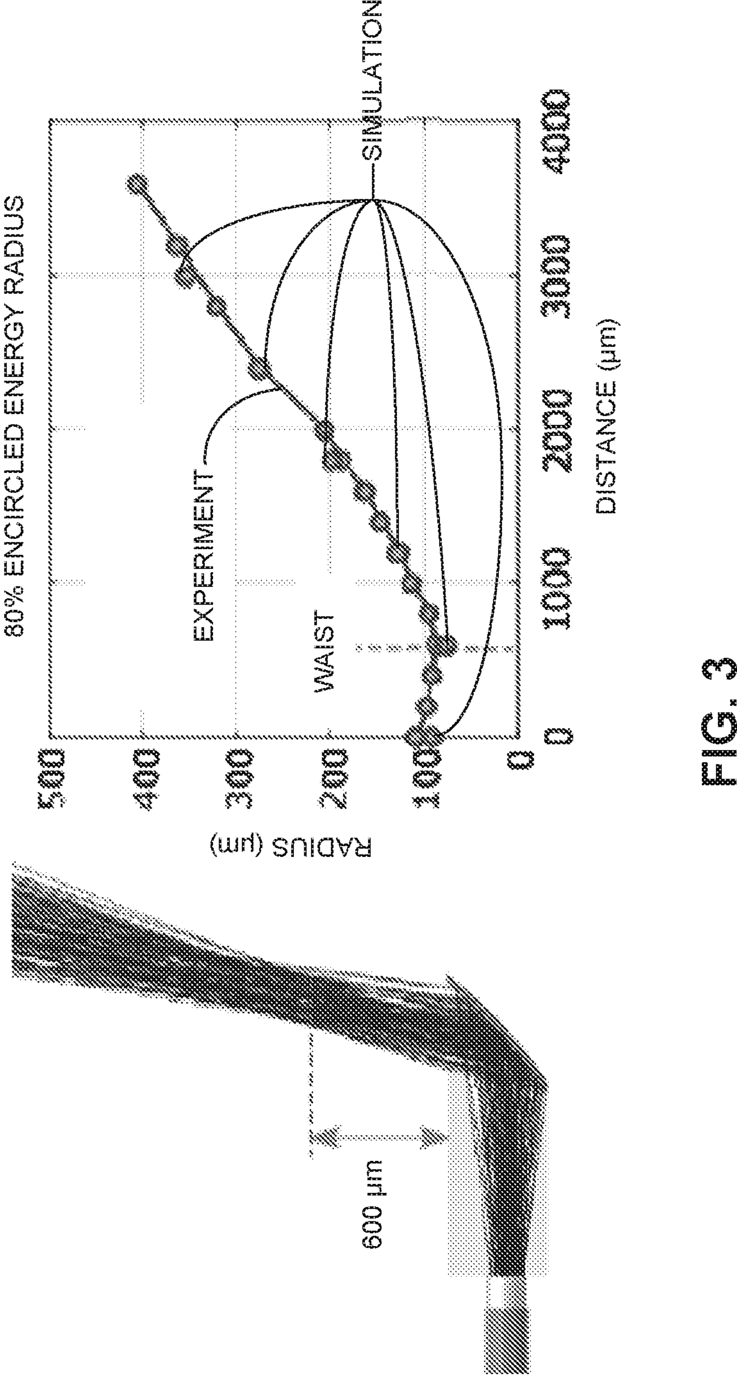
FIG. 3 illustrates beam waist axial position and overall beam diameter as a function of distance in accordance with disclosed embodiments

The beam profile characterization was performed by coupling the fiber optic to an extended light source (L9455-1, Hamamatsu Photonics, Hamamatsu, Japan) to achieve an overfilled launch condition. The beam profile was measured using a 20× microscope objective and a 1,392×1,040 CCD camera (CCE-B013-U, Mightex, Toronto, Canada), leading to a pixel size of 1.047 μm. Note that multimode beams do not necessarily present a Gaussian profile; therefore, the beam size was determined as the 80% encircled energy radius. A Zemax simulation of the beam profile was performed on the fiber and the freeform surface optics model described previously with reference to FIG. 1A, and the 80% encircled energy radius was computed for different detector plane distances. Simulated and experimental data, which are presented in FIG. 3, illustrate a very good agreement on overall beam diameter as a function of distance as well as beam waist axial position. Although the freeform surface was optimized to minimize the beam radius at 1.5 mm distance, the large fiber core to optics aperture ratio is such that the waist is located only 600 μm from the surface of the element.

Figure 4:
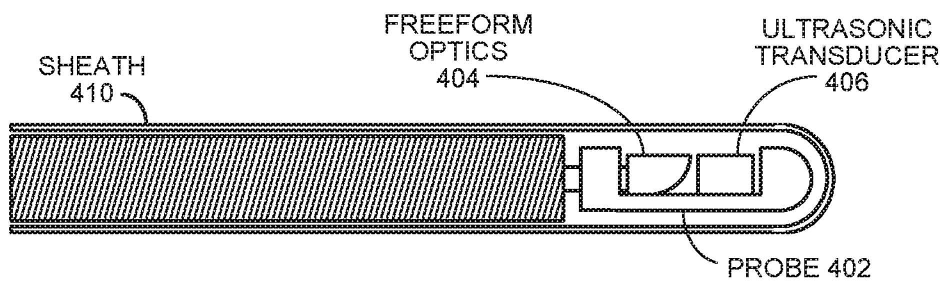
FIG. 4 illustrates integration of a freeform optic into a FLIm-IVUS intravascular catheter in accordance with disclosed embodiments.

Finally, a series of FLIm-IVUS catheters integrating the freeform optics were manufactured and highlighted additional key benefits of the proposed solution. See FIG. 4, which illustrates an integration of the freeform optics 404 into a FLIm-IVUS intravascular catheter probe 402. This freeform optics 404 presents a large 300 μm aperture to enhance fluorescence signal collection and can be integrated into a compact 600 μm diameter, 1.8 mm length probe 402, which also includes an ultrasonic transducer 406. The catheter probe and associated rotating components are surrounded by a non-rotating sheath 410, which is in direct contact with patient. Because the beam is reflected internally on the freeform surface, the element can be easily integrated into an imaging device by potting the freeform optics 404 with adhesive, ensuring a high level of protection. Note that only the fused silica top surface is exposed to the surrounding environment.

Process for Fabricating Micro-Optic Elements

FIG. 5 presents a flowchart illustrating a process for fabricating micro-optic elements in accordance with disclosed embodiments. First, the process creates one or more curved surfaces in a silica wafer, wherein the one or more curved surfaces have a geometry suitable to shape an internal optical beam by reflection (step 502). Next, the process deposits a reflective coating on the silica wafer to provide reflectivity, thereby converting the one or more curved surfaces into one or more internal freeform reflective surfaces (step 504). Finally, the process cuts the silica wafer to obtain one or more micro-optic elements, which are configured to receive an incoming optical beam along a rotational axis of the catheter, wherein each micro-optic element includes a freeform reflective internal surface to reflect the incoming optical beam in a substantially orthogonal direction from the optical axis toward a target location, and wherein the internal reflective surface is shaped to focus the beam so that a resulting beam shape at the target location has a small cross section area and substantially equal axial and transaxial dimensions (step 506).

Figure 6:
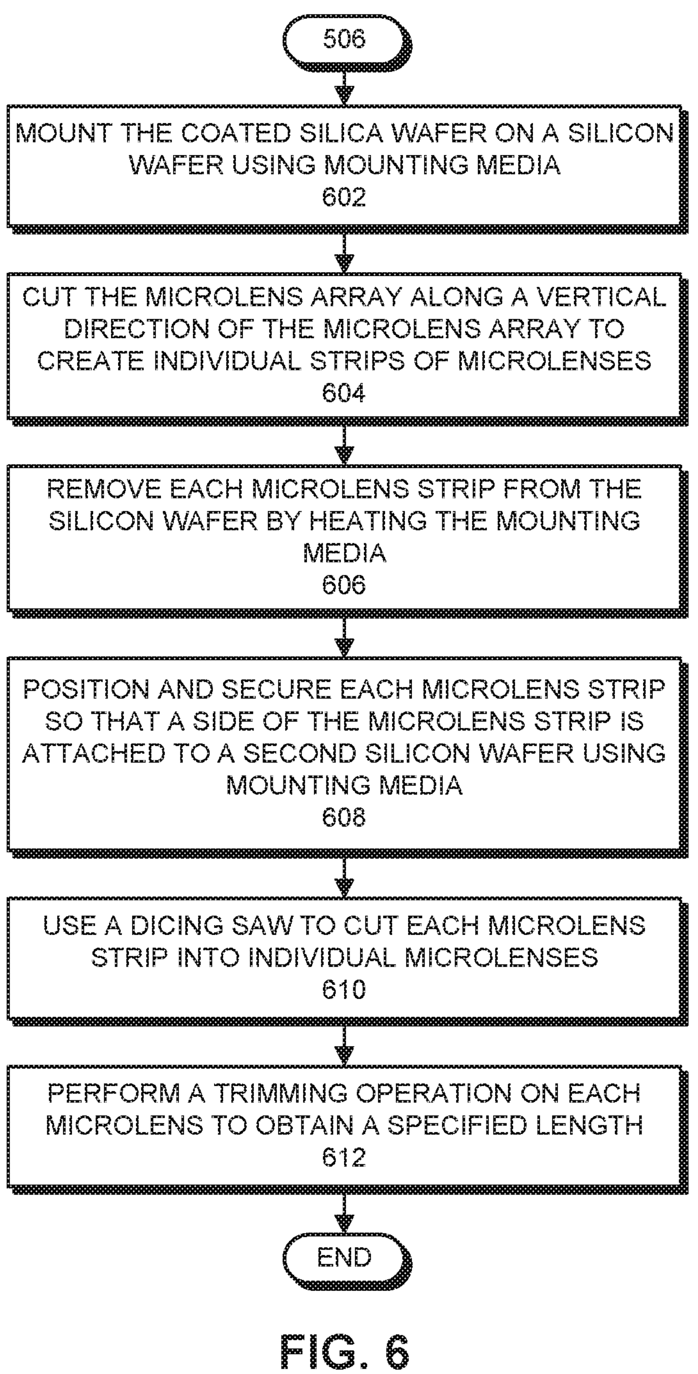
FIG. 6 presents a flowchart illustrating a process for cutting a microlens array to obtain microlenses in accordance with disclosed embodiments.

FIG. 6 presents a flowchart illustrating a process for cutting a microlens array to obtain microlenses in accordance with disclosed embodiments. (This flowchart provides more details about the operations involved in step 506 in the flowchart in FIG. 5.) First, the process mounts the coated silica wafer on a silicon wafer using mounting media (step 602). Then, the process cuts the microlens array along a vertical direction of the microlens array to create individual strips of microlenses (step 604). The process then removes each microlens strip from the silicon wafer by heating the mounting media (step 606). The process then positions and secures each microlens strip so that a side of the microlens strip is attached to a second silicon wafer using mounting media (step 608) The process then uses a dicing saw to cut each microlens strip into individual microlenses (step 610). Finally, the process performs a trimming operation on each microlens to obtain a specified length (step 612).

Figure 7:
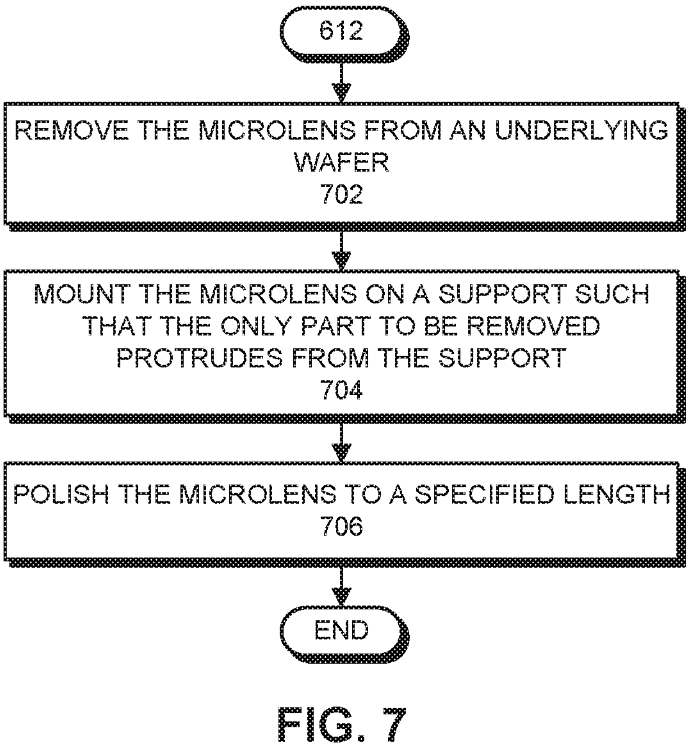
FIG. 7 presents a flowchart illustrating a process for trimming a microlens in accordance with disclosed embodiments.

FIG. 7 presents a flowchart illustrating a process for trimming a microlens in accordance with disclosed embodiments. (This flowchart provides more details about the operations involved in step 612 in the flowchart in FIG. 6.) First, the process removes the microlens from an underlying wafer (step 702). Next, the process mounts the microlens on a support such that the only part to be removed protrudes from the support (step 704). Finally, the process polishes the microlens to a specified length (step 706).

Conclusion

A novel type of side-viewing optics based on a freeform reflective surface has been designed, manufactured and characterized. This new design addresses the shortcomings of ball lens and GRIN distal-end optics and is ideally suited for fluorescence imaging due to its high transmission and low autofluorescence in the UV range. The design of the elements was performed using standard optics simulation software where surrounding elements such as the catheter sheath are easily included. By using optimization techniques, the design of a freeform surface geometry that best fulfills the design requirements and therefore maximizes imaging performances is straightforward. The direct-write laser machining of the optics does not require the upfront investment necessary for alternative techniques, such as grayscale lithography or molding, and can be easily outsourced. Moreover, the manufacturing steps are performed with standard dicing and hand polishing equipment. The use of a temporary adhesive during the dicing and polishing steps is ideally suited to the fixturing of miniature parts and protects the functional surface of the optics so no damage to any of the optics manufactured with this process occurred. By using the above technique, several hundred optics can be manufactured from the same wafer and may include a large variety of alternative designs, making the technique suitable for both research and development and production. The reflective optical coating deposition is done on the wafer, so it is easy and very cost-effective because all optics of a batch can be coated at once. Using different types of reflective coating (metallic/dielectric) allows the optimization of the optics' performance for a specific wavelength range of operation, but good transmission and minimal chromatic aberrations can easily be achieved over the whole UV-to-NIR range. The freeform optics are currently attached to the fiber using adhesive so coupling losses may be higher than monolithic fused ball lens designs. Nonetheless, the ability to freely optimize the reflective surface, the inherently broadband design with minimal chromatic aberrations, and the robustness and ease of integration enabled by the reflection on a protected internal surface make it an ideal component for intravascular FLIm. This broadband design may also lead to improvements in multimodal techniques spanning a large wavelength range, such as the combination of fluorescence and OCT.

Various modifications to the disclosed embodiments will be readily apparent to those skilled in the art, and the general principles defined herein may be applied to other embodiments and applications without departing from the spirit and scope of the present invention. Thus, the present invention is not limited to the embodiments shown, but is to be accorded the widest scope consistent with the principles and features disclosed herein.

The foregoing descriptions of embodiments have been presented for purposes of illustration and description only. They are not intended to be exhaustive or to limit the present description to the forms disclosed. Accordingly, many modifications and variations will be apparent to practitioners skilled in the art. Additionally, the above disclosure is not intended to limit the present description. The scope of the present description is defined by the appended claims.

What is claimed is:

1. A method for manufacturing a side-viewing micro optic for a catheter, comprising:

creating one or more curved surfaces in a silica wafer, wherein the one or more curved surfaces have a geometry suitable to shape an internal optical beam by reflection;

depositing a reflective coating on the silica wafer to provide reflectivity, thereby converting the one or more curved surfaces into one or more internal freeform reflective surfaces; and cutting the silica wafer to obtain one or more micro-optic elements, which are configured to receive an incoming optical beam along a rotational axis of the catheter, wherein each micro-optic element includes a freeform reflective internal surface to reflect the incoming optical beam in a substantially orthogonal direction from the optical axis toward a target location, and wherein the freeform reflective internal surface is shaped to focus the incoming optical beam so that a resulting beam shape at the target location has substantially equal axial and transaxial dimensions.

2. The method of claim 1, wherein the one or more curved surfaces are created using direct laser machining.

3. The method of claim 1, wherein the one or more curved surfaces are created using a grayscale lithography technique.

4. The method of claim 1, wherein the reflective coating is not deposited in cases where a total internal reflection with a surrounding medium is sufficient to reflect the optical beam.

5. The method of claim 1, wherein creating the one or more curved surfaces involves creating a microlens array comprising a large number of curved surfaces organized in a rectangular pattern on the silica wafer.

6. The method of claim 5, wherein the cutting of the silica wafer is performed using a dicing saw by:

mounting the coated silica wafer on a silicon wafer using mounting media;

cutting the microlens array along a vertical direction of the microlens array to create individual strips of microlenses;

removing each microlens strip from the silicon wafer by heating the mounting media;

positioning and securing each microlens strip so that a side of the microlens strip is attached to a second silicon wafer using mounting media;

using a dicing saw to cut each microlens strip into individual microlenses; and performing a trimming operation on each microlens.

7. The method of claim 6, wherein performing the trimming operation on each microlens comprises:

removing the microlens from an underlying wafer;

mounting the microlens on a support such that the only part to be removed protrudes from the support; and polishing the microlens to a specified length.

8. The method of claim 1, wherein the cutting of the silica wafer is performed using a laser.

9. The method of claim 1, wherein the cutting of the silica wafer is performed in a single operation by tilting a cutting plane.

10. The method of claim 6, further comprising polishing an upper surface of each microlens to limit scattering caused by roughness created by the dicing process.

11. The method of claim 2, wherein while using the direct laser machining process to create the microlens array, the method ensures that a spacing between microlenses corresponds to a kerf width of a blade of the dicing saw.

12. The method of claim 1, wherein the cutting of the silica wafer comprises:

mounting the silica wafer with the reflective coating on a silicon wafer;

cutting the silica wafer to create individual strips;

removing each strip from the silicon wafer;

attaching each strip to a second silicon wafer; and using a dicing saw to cut each strip to obtain the one or more micro-optic elements.

13. A method for manufacturing a side-viewing micro optic for a catheter, comprising:

creating one or more curved surfaces in a silica wafer, wherein the one or more curved surfaces have a geometry suitable to shape an internal optical beam by reflection;

depositing a reflective coating on the silica wafer to provide reflectivity, thereby converting the one or more curved surfaces into one or more internal freeform reflective surfaces;

cutting the silica wafer to obtain one or more micro-optic elements, which are configured to receive an incoming optical beam along a rotational axis of the catheter, wherein each micro-optic element includes a freeform reflective internal surface to reflect the incoming optical beam in a substantially orthogonal direction from the optical axis toward a target location, and wherein internal reflective-freeform reflective internal surface is shaped to focus the light incoming optical beam so that a resulting beam shape at the target location has substantially equal axial and transaxial dimensions; and wherein creating the one or more curved surfaces involves creating a microlens array comprising a large number of curved surfaces organized in a rectangular pattern on the silica wafer; and wherein the cutting of the silica wafer is performed using a dicing saw by:

mounting the coated silica wafer on a silicon wafer using mounting media, cutting the microlens array along a vertical direction of the microlens array to create individual strips of microlenses, removing each microlens strip from the silicon wafer by heating the mounting media, positioning and securing each microlens strip so that a side of the microlens strip is attached to a second silicon wafer using mounting media, using a dicing saw to cut each microlens strip into individual microlenses, and performing a trimming operation on each microlens.

14. A method for manufacturing a side-viewing micro optic for a catheter, comprising:

creating one or more curved surfaces in a silica wafer, wherein the one or more curved surfaces have a geometry suitable to shape an internal optical beam by reflection;

depositing a reflective coating on the silica wafer to provide reflectivity, thereby converting the one or more curved surfaces into one or more internal freeform reflective surfaces;

cutting the silica wafer to obtain one or more micro-optic elements, which are configured to receive an incoming optical beam along a rotational axis of the catheter, wherein each micro-optic element includes a freeform reflective internal surface to reflect the incoming optical beam in a substantially orthogonal direction from the optical axis toward a target location, and wherein the freeform reflective internal surface is shaped to focus the incoming optical beam so that a resulting beam shape at the target location has substantially equal axial and transaxial dimensions; and wherein the cutting of the silica wafer is performed in a single operation by tilting a cutting plane.

* * * * *